United States Patent [19]

Arkles et al.

[11] Patent Number: 4,596,882
[45] Date of Patent: * Jun. 24, 1986

[54] MODIFIED SILACROWN ETHERS AND METHODS OF MAKING SAME

[75] Inventors: Barry C. Arkles, Oreland; Kevin M. King, Levittown, both of Pa.

[73] Assignee: Petrarch Systems Inc., Bristol, Pa.

[ * ] Notice: The portion of the term of this patent subsequent to Dec. 2, 1999 has been disclaimed.

[21] Appl. No.: 579,294

[22] Filed: Feb. 15, 1984

Related U.S. Application Data

[63] Continuation of Ser. No. 431,940, Sep. 30, 1982, abandoned, which is a continuation-in-part of Ser. No. 323,629, Nov. 23, 1981, Pat. No. 4,362,884.

[51] Int. Cl.$^4$ ............................ C07F 7/08; C07F 7/10; C07F 7/18
[52] U.S. Cl. .................................... 556/423; 556/416; 556/446
[58] Field of Search ........................ 556/416, 446, 423

[56] References Cited

U.S. PATENT DOCUMENTS 4,362,884 12/1982 Arkles .................................. 556/446

OTHER PUBLICATIONS

C. J. Pederson, *J. Am. Chem. Soc.*, 89,7017 (1967).
T. G. Waddell, D. E. Leyden, *J. Org. Chem.*, 46,2406–7, (1981).
R. Kieble, C. Burkhard, *J. Am. Chem. Soc.*, 69, 2689 (1947).
PCR Research Chemicals, Inc., technical bulletin, Crown Ethers, Von Hoang Thi Phung, Pham Ba Chi, F. Kober, *Z. Anorg. Allg. Chem.*, 472,75–82 (1981), (German Language–no translation).

*Primary Examiner*—Paul F. Shaver
*Attorney, Agent, or Firm*—Panitch Schwarze Jacobs & Nadel

[57] ABSTRACT

Modified silacrown ethers are formed having the general formula:

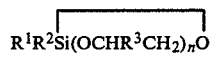

wherein $R^1$ and $R^2$ are organic radicals, hydrogen or groups which actively assist in the complexing of metal cations, n is an integer between 3 and 10 inclusive, and $R^3$ is hydrogen or lower alkyl. These modified silacrown ethers are prepared by reacting a polyalkylene glycol with substituted silanes under conditions promoting cyclization over polymerization. The modified silacrown ethers are useful for forming cation complexes and promoting anionic reactions, particularly in phase transfer reactions either in solution or immobilized on siliceous supports.

11 Claims, 3 Drawing Figures

MODIFIED SILACROWN ETHERS AND METHODS OF MAKING SAME

CROSS REFERENCE TO RELATED APPLICATION

This application is a continuation of copending U.S. Application Ser. No. 431,940, filed Sept. 30, 1982, now abandoned, which is a continuation-in-part of copending U.S. Application Ser. No. 323,629, filed Nov. 23, 1981, now U.S. Pat. No. 4,362,884 by Barry C. Arkles for "Silacrown Ethers, Methods of Making Same, and Use as Phase-Transfer Catalysts".

BACKGROUND OF THE INVENTION

"Silacrowns" or "silacrown ethers" are macrocyclic multidentate ethers which resemble in structure and complexation properties a class of compounds known as "crown ethers", but differ in the replacement of a —$C_2H_4$— group by a silicon group. U.S. Pat. No. 4,362,884 discloses the preparation and uses of such compounds. The present invention is directed to the preparation of modified silacrowns which have the ability to assist in the complexation of various cations.

Since 1967 when C. Pedersen discovered the crown ethers, literally thousands of applications have developed in which their ability to complex metal ions, solvate inorganic and organic salts in polar and non-polar solvents, and facilitate anionic reactions have been exploited. Much of this work has been reviewed in *Synthetic Multidentate Macrocyclic Compounds* by R. Izatt and J. Christiansen, Academic Press 1978. Two obstacles have prevented their wider utilization, particularly in commercial processes: current synthetic methods are extremely costly, and the materials have generally high levels of toxicity. These factors, coupled with the difficulty in separating the crown ethers during preparation by processes other than distillation, have hindered wider applications. An example is the acylation step in penicillin synthesis.

Although cyclic polyethyleneoxysilanes have been previously reported, the ring structures have fewer members than the silacrowns. The inside diameters of the ring structures are clearly smaller than lithium ions. R. Krieble, C. Burkhard, *J. Am. Chem. Soc.* 69, 2689 (1947). Because the ring structures are so small, these compounds cannot form complexes with cations.

As disclosed in U.S. Pat. No. 4,362,884, silacrowns exhibit complexation properties remarkably similar to crown ethers. A specific example is dimethylsila-14-crown-5.

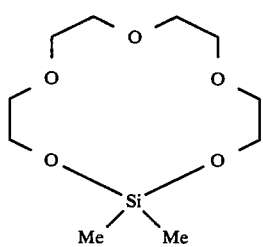

FIG. 1

The name indicates the substituents on silicon, the number of members in the ring, and the number of oxygens. This compound may be compared to the corresponding crown ether, 15-crown-5. Although there is one less member in the ring for the silacrown, the longer silicon-oxygen bonds result in an O-Si-O unit that has 75 percent of the bond length of an O-$CH_2$-$CH_2$-O unit. Simple addition of bond lengths indicates an overall reduction in macrocycle circumference of 4.5 percent when compared to 15-crown-5.

Hereinafter, the absence of a prefix in a silacrown name indicates "dimethyl". Thus, dimethylsila-14-crown-5 may be abbreviated sila-14-crown-5.

The silacrowns are generally colorless, odorless liquids of moderate viscosity. They appear to have the ability to form stable molecular complexes with alkaline or alkaline earth salts in solution as well as in the solid state, behaving as phase transfer catalysts. Solvation of the metal ions leaves anions unencumbered, enabling them to act as potent bases and nucleophiles. This is demonstrated in a number of processes including nitrile, acetate, nitrite, fluoride and iodide displacements. Oxidations with permanganate and chromate are facilitated.

Certain silacrowns have the ability to react with siliceous materials, forming immobilized silacrowns. The immobilized silacrowns demonstrate the same ability to catalyze reactions as their unbound counterparts. They are particularly useful in liquid/liquid phase transfer reactions.

BRIEF SUMMARY OF THE INVENTION

The modified silacrown ethers of the present invention have the general structure:

$$R^1R^2Si(OCHR^3CH_2)_nO$$

wherein n is an integer from 3 to 10 inclusive, $R^1$ and $R^2$ are selected from the group consisting of hydrogen, alkyl, unsaturated alkyl, alkoxy, aryl, aminoalkyl, cyanoalkyl and ethyleneoxy groups, although other organic radicals may also be substituted; and $R^3$ is hydrogen or lower alkyl. However, when $R^3$ is hydrogen, at least one of $R^1$ and $R^2$ is an aminoalkyl, cyanoalkyl or ethyleneoxy group. Thus, the silacrowns in which $R^3$ is hydrogen and both $R^1$ and $R^2$ are organic radicals selected from the group consisting of hydrogen, alkyl, unsaturated alkyl, alkoxy and aryl, are disclosed and claimed in U.S. Pat. No. 4,362,884.

The modified silacrowns are produced by reacting a polyalkylene glycol having the general formula:

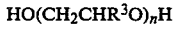

$$HO(CH_2CHR^3O)_nH$$

wherein n is an integer between 3 and 10 inclusive, with a silane having the general formula:

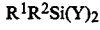

$$R^1R^2Si(Y)_2$$

under conditions which promote cyclization over polymerization, wherein Y is selected from the group consisting of alkoxy, acyloxy, amino and chloro groups, and $R^1$, $R^2$ and $R^3$ are as described above.

As with the silacrown ethers of U.S. Pat. No. 4,362,884, the modified silacrowns of the present invention may be used to catalyze anionic displacement reactions. The modified silacrowns act to complex various metal cations. Immobilized silacrowns formed by the reaction of siliceous materials and silacrown ethers may be used to catalyze liquid/liquid phase transfer reactions.

DETAILED DESCRIPTION OF PREFERRED EMBODIMENTS

Figure 1:
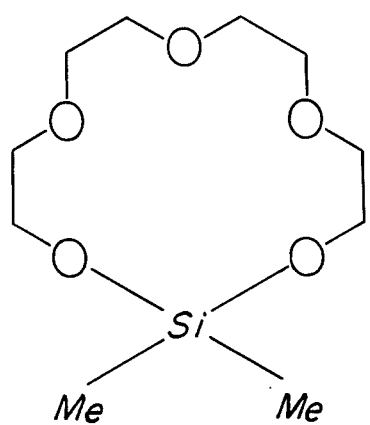

Silacrown ethers may be described as cyclic diesters of a substituted silicon atom and polyethylene glycol. The present invention involves significant modifications of these basic compositions by substitution either on the silicon atom or on the ethyleneoxy groups or both.

The regular substitution of alkyl groups on the carbon atoms of the ethyleneoxy groups has been found to significantly enhance the non-polar character of the exterior of the silacrown shell. Such a regular substitution is achieved by substituting another polyakylene glycol for the polyethylene glycol in the transesterification reaction. In the preferred embodiment, methyl groups are substituted on carbon atoms of the ethyleneoxy groups by simply substituting polypropylene glycol for polyethylene glycol in the transesterification reaction.

The modified silacrowns of this type may be readily prepared from commercially available polyalkylene glycols by transesterification with a silane according to the following reaction:

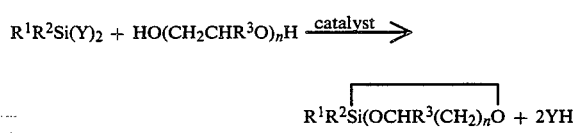

Reaction conditions must be selected to promote cyclization in preference to polymerization. The reaction may be catalyzed by a variety of transesterification catalysts including methylsulfonic acid, toluenesulfonic acid, sodium, titanates and a variety of other materials known in the literature. Titanates are generally preferred. The reactants are combined and approximately 80-95 percent of the alcohol by-product (where Y is alkoxy) is slowly distilled from the reaction mixture. If the silacrown being prepared contains a moiety which does not have a great thermal stability, such as a vinyl group, it is useful to add a higher boiling solvent such as toluene.

The silacrown is removed from the reaction mixture by distillation, shifting the equilibrium from polymer to silacrown. It appears that there is some molecular rearrangement from polymer to silacrown during the course of distillation in the presence of transesterification catalysts that results from this preferential removal of the more volatile silacrowns from the reaction mixture.

The Y group is preferably alkoxy, such as ethoxy or methoxy, so that the alcohol by-product may be readily distilled. The direct interaction of chloro-, amino-, or acyloxysilanes with polyalkylene glycols can also lead to the desired products, but in significantly lower yield.

The modified silacrown ethers prepared in accordance with the above reaction correspond to the general formula:

wherein:
$R^1$ and $R^2$ are organic radicals or hydrogen;
$R^3$ is lower alkyl, preferably methyl; and
n is an integer between 3 and 10 inclusive.

Specific examples of the R groups are methyl, ethyl, benzyl, phenyl, cyclohexyl and phenethyl which may be utilized to alter solubility characteristics. Alkoxy, vinyl and aminoalkyl groups may be employed to enable coupling to a substrate. Within the scope of this invention, it is obvious that any R group that is compatible with the methods of synthesis cited, and which does not alter the crown structure, is acceptable.

The value of n is limited by the ability to recover the silacrown product by distillation during synthesis. For n values above 10, the silacrown is impossible to separate from the reaction mixture. The preferred values of n are 3-7.

Another significant modification which can be made to the silacrown ethers of U.S. Pat. No. 4,362,884 is the substitution on the silicon atom of a group which actively assists in the complexing of various metal cations. That is, at least one of the $R^1$ and $R^2$ substituents in the above formulas may be substituted with a group such as an aminoalkyl, cyanoalkyl nitrile or ethyleneoxy group. Preferred examples of each of these groups are the following:

(1) $-CH_2CH_2CH_2NHCH_2CH_2NH_2$
   N-(2-aminoethyl)-3-aminopropyl
(2) $-CH_2CH_2CH_2CN$
   3-cyanopropyl
(3) $-OCH_2CH_2OCH_2CH_2OCH_2CH_2CH_2OCH_3$
   triethylene glycol mono methyl ether
or
   1,4,7,10-tetraoxaundecyl respectively. Other groups of this type will be evident to those of ordinary skill in the art based upon the present disclosure.

The modified silacrowns of this type may be formed by the same type of transesterification reaction as indicated above between a polyalkylene glycol and a substituted silane, preferably an alkoxy silane. However, where an aminoalkyl group is used as a substituent on the silicon atom, no separate catalyst is generally necessary, since amine groups catalyze the transesterification reaction. Also, where an amine group is used as a substituent, it is not generally possible to use a chlorosilane since undesired chloroamines will be formed. That is, in general, a particular silane and substituents thereon must be selected so that the hydrolyzable group on the silane does not react with one of the substituents to be included in the final product.

It will be understood that both the $R^1$ and $R^2$ groups could be substituted with groups which actively assist in complexing metal cations. It will also be understood that both of the modifications proposed by the present invention could be carried out on the same modified silacrown, so that there are alkyl groups on the ethyleneoxy groups of the silacrown ring as well as complexing substituents on the silicon atom.

Particular cation complexes and anionic reactions which may be promoted using the modified silacrown compounds of the present invention are exemplified in U.S. Pat. No. 4,362,884. In addition, the silicon atom substituted compounds of the present invention are particularly useful in complexing metal cations such as barium, iron, copper and cadmium as well as lithium, sodium and potassium.

The present invention may be illustrated in more detail by reference to the following specific non-limiting examples:

EXAMPLE I

Preparation of Dimethylsila-3,6,9-trimethyl-11-crown-4

Figure 2:
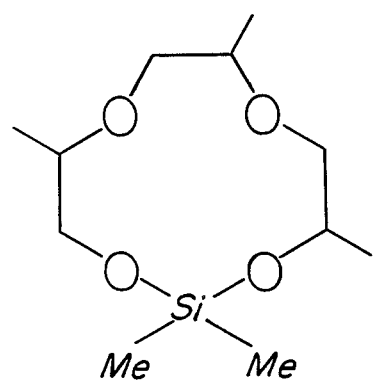

Equimolar amounts of dimethyldiethoxysilane and tripropylene glycol and 0.5 wt % tetrabutyltitanate were charged in a single neck flask equipped with magnetic stirrer, heating mantle and a distillation head. The mixture was stirred overnight at 40° C. 1.8 molar equivalents of ethanol were distilled from the mixture. The mixture was then distilled under vacuum yielding 69% of the title compound (b.p. 125°–9° C./0.2–0.3 mm Hg), whose structure is illustrated below in FIG. 2.

FIG. 2

EXAMPLE II

Preparation of [N-(2-aminoethyl)-3-aminopropyl]methylsila-14-crown-5

Figure 3:
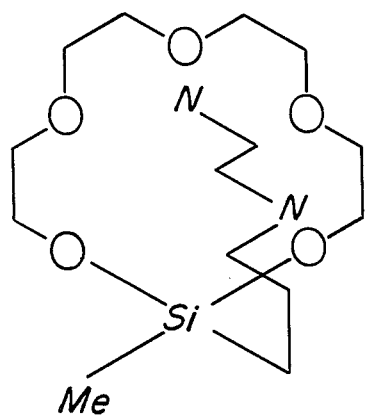

One mole each of N-(2-aminoethyl)-3-aminopropyl-methyldimethoxysilane and tetraethylene glycol were charged in a one liter flask. About 1.7 moles of methanol were slowly distilled from the mixture. (No titanate was used in this procedure, since the amine groups catalyzed the transesterification). The product was recovered from the mixture in the fraction distilled at 221°–8° C./0.2 mm Hg. A portion of the material in the distillation flask degraded to a resin during the distillation. Recovered product represented approximately 35% yield, and the product is illustrated below in FIG. 3.

FIG. 3

EXAMPLE III

In order to test the complexation properties of the compound of Example II above, three beakers were prepared containing 50 mls of chlorobenzene and 1 g of cuprous chloride. Cuprous chloride is a pale green solid which is essentially insoluble in chlorobenzene. 1 ml of dimethylsila-14-crown-5 was added to one beaker. No change was observed. 5 mls of ethylenediamine was added to the second beaker. The cuprous chloride assumed a pale blue color, but the chlorobenzene remained clear. To the third beaker 1 ml of the compound of Example II was added. Within seconds the chlorobenzene assumed a pale blue coloration. The color intensified over 30 minutes to give a deep brilliant blue, indicating the presence of a soluble copper complex.

The present invention may be embodied in other specific forms without departing from the spirit of essential attributes thereof and, accordingly, reference should be made to the appended claims, rather than to the foregoing specification, as indicating the scope of the invention.

I claim:

1. Compounds of the structure $$R^1R^2Si(OCHR^3CH_2)_nO$$

wherein n is an integer from 3 to 10 inclusive, $R^1$ and $R^2$ are selected from the group consisting of alkyl, unsaturated alkyl, alkoxy, aryl, hydrogen and moieties which actively assist in complexing metal cations, and $R^3$ is selected from the group consisting of hydrogen and lower alkyl, but at least one of $R^1$ and $R^2$ is a moiety which actively assists in complexing metal cations.

2. Compounds according to claim 1 wherein $R^3$ is methyl.

3. Compounds according to claim 1 wherein said moiety which actively assists in complexing metal cations is selected from the group consisting of diaminoalkyl, cyanoalkyl and ethyleneoxy groups.

4. Compounds according to claim 3 wherein one of $R^1$ and $R^2$ is selected from the group consisting of alkyl, unsaturated alkyl, alkoxy, aryl and hydrogen.

5. Compounds according to claim 3 wherein said moiety is selected from the group consisting of —$CH_2CH_2CH_2CN$; —$CH_2CH_2CH_2NHCH_2CH_2NH_2$ and —$OCH_2CH_2OCH_2OCH_2CH_2OCH_3$.

6. [N-(2-aminoethyl)-3-aminopropyl]methylsila-14-crown-5.

7. A method for producing modified silacrown ethers by a transesterification reaction between a polyalkylene glycol having the general formula $$HO(CH_2CHR^3O)_nH$$

wherein n is an integer from 3 to 10 inclusive and $R^3$ is hydrogen or lower alkyl, and a silane having the general formula $$R^1R^2Si(Y)_2$$

under conditions which promote cyclization over polymerization, wherein Y is selected from the group consisting of alkoxy, acyloxy, amino and chloro, and $R^1$ and $R^2$ are selected from the group consisting of alkyl, unsaturated alkyl, alkoxy, aryl, hydrogen and moieties which actively assist in complexing metal cations, but at least one of $R^1$ and $R^2$ is a moiety which actively assists in complexing metal cations.

8. A method according to claim 7 wherein said glycol is polypropylene glycol.

9. A method according to claim 7 wherein the reaction uses a separate catalyst.

10. A method according to claim 7 wherein said moiety which actively assists in complexing metal cations is selected from the group consisting of aminoalkyl, cyanoalkyl and ethyleneoxy groups.

11. A method according to claim 10 wherein said moiety is an amine group which also catalyzes the esterification reaction.

* * * * *